United States Patent [19]

Hansen et al.

[11] 4,092,574
[45] May 30, 1978

[54] AUTOMATIC REMOTE CONTROLLED OPTHALMIC REFRACTING CHART PROJECTOR

[75] Inventors: Donald H. Hansen; Morey H. Waltuck, both of Williamsville, N.Y.

[73] Assignee: American Optical Corporation, Southbridge, Mass.

[21] Appl. No.: 748,601

[22] Filed: Dec. 8, 1976

[51] Int. Cl.² .............................................. G05B 11/14
[52] U.S. Cl. ...................................... 318/265; 318/467
[58] Field of Search ................. 351/30; 318/264, 265, 318/466, 467

[56] References Cited

U.S. PATENT DOCUMENTS

| | | | |
|---|---|---|---|
| 2,802,978 | 8/1957 | Legros | 318/265 X |
| 3,437,895 | 4/1969 | Peters | 318/265 X |
| 3,614,578 | 10/1971 | Woodward et al. | 318/467 X |
| 3,648,139 | 3/1972 | Friedman | 318/265 |
| 3,655,276 | 4/1972 | Wilkinson | 351/30 |

Primary Examiner—Robert K. Schaefer
Assistant Examiner—W. E. Duncanson, Jr.
Attorney, Agent, or Firm—Jeremiah J. Duggan; Howard R. Berkenstock, Jr.

[57] ABSTRACT

An ophthalmic refracting chart projector having rotary slide discs, the images on which are projected on a screen, having remote operating controls permitting selective showing of the slides in selectable sequence.

3 Claims, 9 Drawing Figures

FIG. 9

AUTOMATIC REMOTE CONTROLLED OPTHALMIC REFRACTING CHART PROJECTOR

BACKGROUND OF THE INVENTION

The present invention relates to projectors for ophthalmic refracting charts, and specifically to such a projector having a remote control unit which permits selective showing of the refracting chart slides according to a sequence selected by an operator through the remote control.

In the field of ophthalmic refraction, it has been known to use projectors incorporating slides having imaged thereon, the various charts useful to the professional conducting eye examinations. These projector devices represent substantial improvement in patient refraction over the old wall charts long used. Typical of such projectors were the early types having a plurality of slides or targets disposed in a linear relationship and moved back or forth, up or down relative to the projecting light path so as to be selectively positioned on the viewing screen. In these projectors, the selection of slides was done manually, often with difficulty in locating and precisely positioning the desired slide for viewing.

In later instruments, such as illustrated in U.S. Pat. No. 3,655,276 (commonly owned by the assignee of the present invention), the slides were placed on circular discs, which were rotated by a control which might be located remotely from the projector either in an automatic mode or in an incremental mode. In the automatic mode, the slides were sequentially shown, according to their placement on one or more of the slide discs. In the incremental mode, the slides were moved to the next sequential position on a disc. Often multiple discs were provided in the slide magazine and when the first disc had completed a revolution, a second would be picked up and rotated through its positions, and so on until all discs had rotated through the numerous positions. As may be recognized, once a particular slide had been passed, either manually or automatically, the entire sequence might have to be passed to return. Also, the operator would have to step through the slide discs to select a particular one for viewing.

The present invention provides a refracting chart projector having a remote control wherein preferably the entire selection of available slides is viewable on the face of the control in the form of a series of selector buttons, and the operator may select according to this desired sequence the particular slide charts to form the refracting examination.

Other objects, advantages, and features of the invention will become apparent from the following description of the invention as illustrated in the embodiment explained.

SUMMARY OF THE INVENTION

The present invention is embodied in and includes a slide projector for ophthalmic refracting charts which is remote controlled thereby enabling greater flexibility and effectiveness to the ophthalmic professional using the chart projector. The slide projector includes a plurality of rotatable coaxial discs, each defining a plurality of slide apertures disposed peripherally around the disc and positionable one at a time in the optical axis of the projector. The discs are each interconnected to a driving motor for rotation with the control means of the motor effective to cause continuous or incremental rotation in response to slide selection at a master keyboard. There is included multiplexing means dedicated to each of the switches of the keyboard for slide apertures, a free running counter to sample the state of the switches, latching means connected to the multiplexers for recording the state of the switches. Comparators take the indication of the latches and compare it to the relative position of the discs as indicated through an up/down counter and input it to the control circuit for the disc driving motors.

In preferred embodiments of the invention, additional circuits are included which provide indicator light illuminations for certain of the functions of the projector as indexing of the discs takes place and also, the disc driving motors are controlled to always select the shortest route to drive to the newly selected position. Additional features of the invention are provided in an off-/on latching circuit which causes the discs to index to a predetermined position on actuation of the switch (preferably a "zero" position).

These and other objects and features of the invention will be evident upon reference to the following specification.

DESCRIPTION OF THE DRAWINGS

FIG. 9 is an electrical diagram representing the control circuits for the projector and part of the present invention.

DESCRIPTION OF A PREFERRED EMBODIMENT

Figure 1:
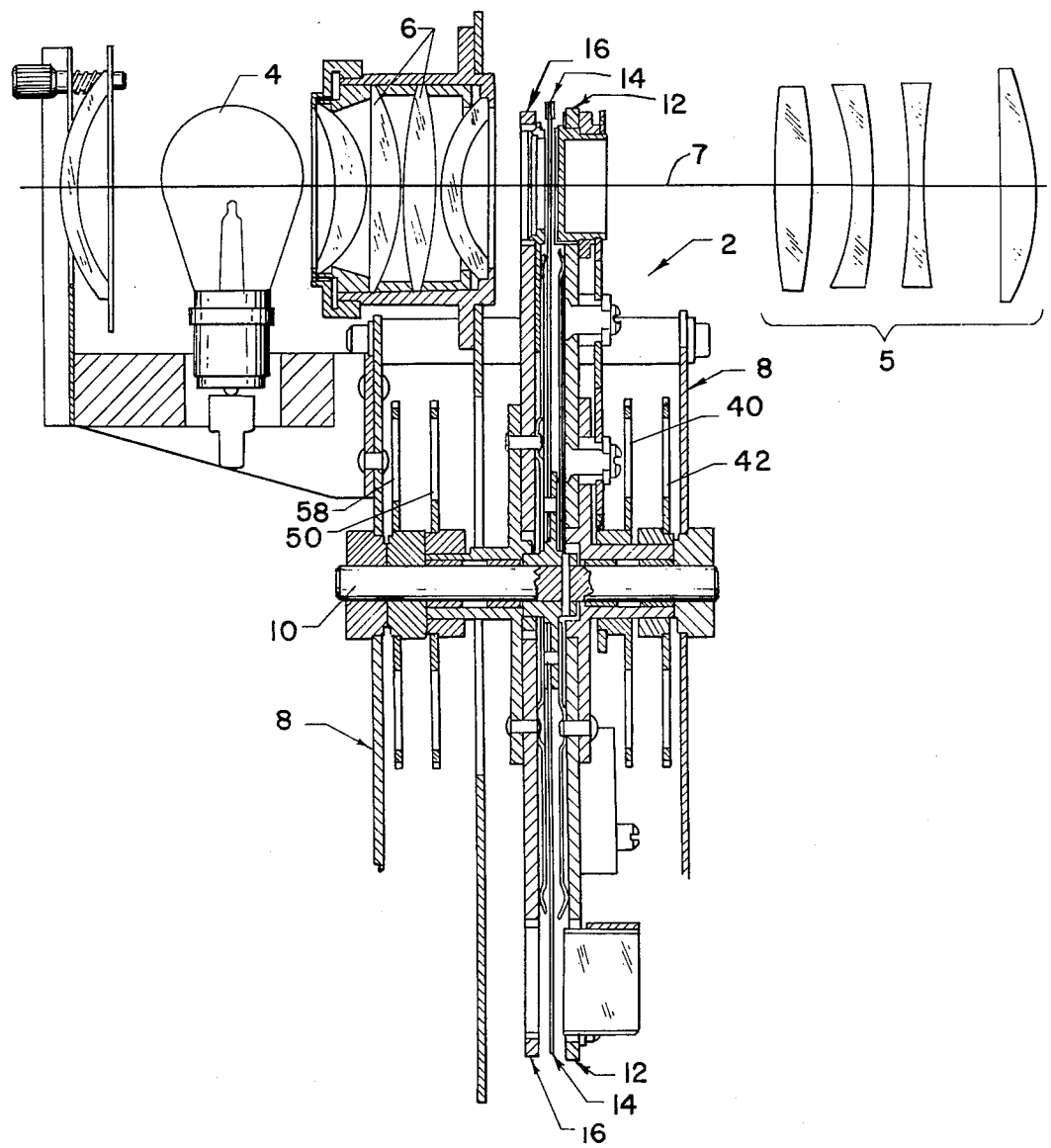
FIG. 1 is a side sectional view of a part of a refracting chart projector according to the present invention.

Referring now to FIG. 1, there is shown a part of a refracting chart projector, generally represented by reference numeral 2. This type of chart projector is shown and described in greater detail in the aforementioned U.S. Pat. No. 3,655,276, however is included herein to assist in a better understanding of the control according to the invention. Projector 2 includes a light 4 disposed relatively in line with a lens system 6 forming therewith means for illuminating and projecting an image from a chart slide (subsequently described). A frame composed of several members 8 supports the structural apparatus of the projector. Disposed therein is a rotatable shaft 10, having mounted thereon rotatable slide chart-carrying discs, e.g. 12, 14 and 16.

Figure 3:
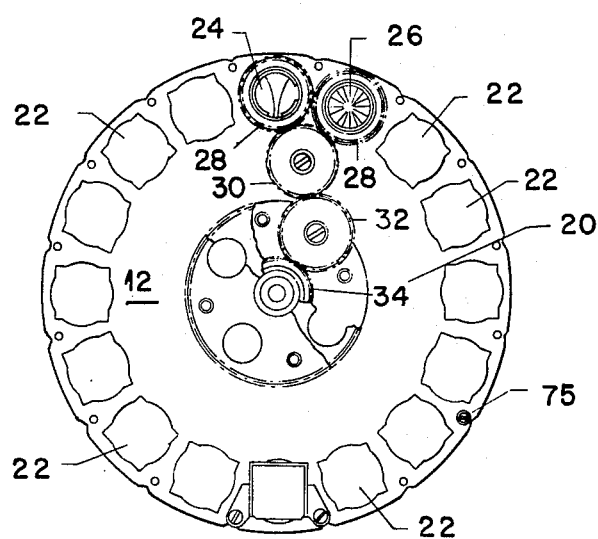
FIGS. 3 and 4 are end and side views respectively of a part of the apparatus shown in FIG. 1.
Figure 4:
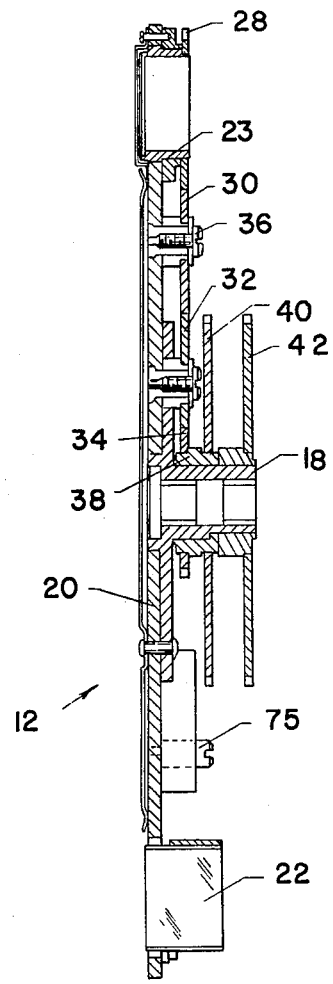

Referring now to FIGS. 3 and 4, disc 12 is shown including bearing member 18 and a disc plate portion 20, integral therewith. Plate 20 defines a plurality of apertures 22 disposed around its periphery for the accomodation of slides. Set into several of these apertures 22 as desired, are rotatable cells 23 containing slides on charts such as a paraboline chart 24 and astigmatic or "sun burst" chart 26. Cells 23 may be rotatably mounted within apertures 22 having an integral and concentric spur gear 27 which may be rotatable in its entirety with only the pointer rotatable relative to a stationary astigmatic chart 26. Disc plate 26 may serve as a mounting plate for a gear train including gears 30 and 32, gear 30 being in mesh with gear 28. Gear 32 meshes with gear 30 and further with spur gear 34 which is rotatably disposed about and preferably concentric with shaft bearing 18. Gears 30 and 32 are mounted relative to plate 20 by suitable fasteners as shown at 36. Spur gear 34 is preferably integrally mounted with a bearing member 38, which is also rotatable about bearing 18, and, in turn, integral with another gear 40, axially disposed and concentric with gear 34. Thus, gear 40, operating through gear 34, rotates gears 32 and 30 and ultimately gears 28 to rotate cells 23 to vary the axis of chart 24 and the pointer relative to chart 26, forming means to keep pointer in line with the vertical axis of paraboline chart eg. to cause pointer and paraboline chart 24 to indicate the same angular displacement when shown to the patient. A gear 42, similar to gear 40, and coaxial therewith is mounted integrally with bearing 18 so as to be rotatable with bearing and plate 20.

Figure 5:
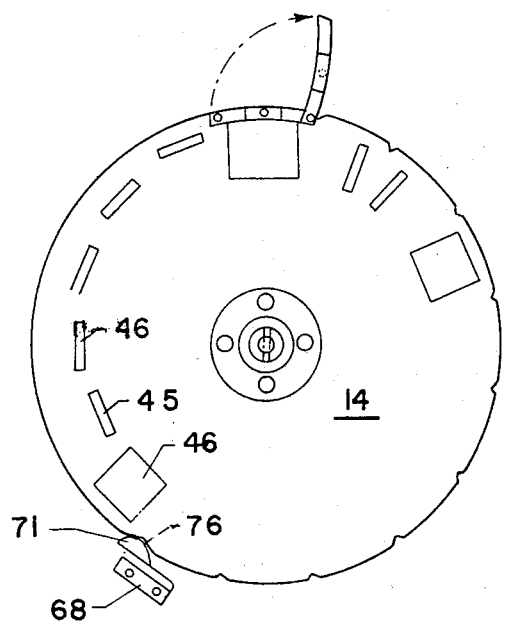
FIGS. 5 and 6 are end and side views respectively of another part of the apparatus shown in FIG. 1.
Figure 6:
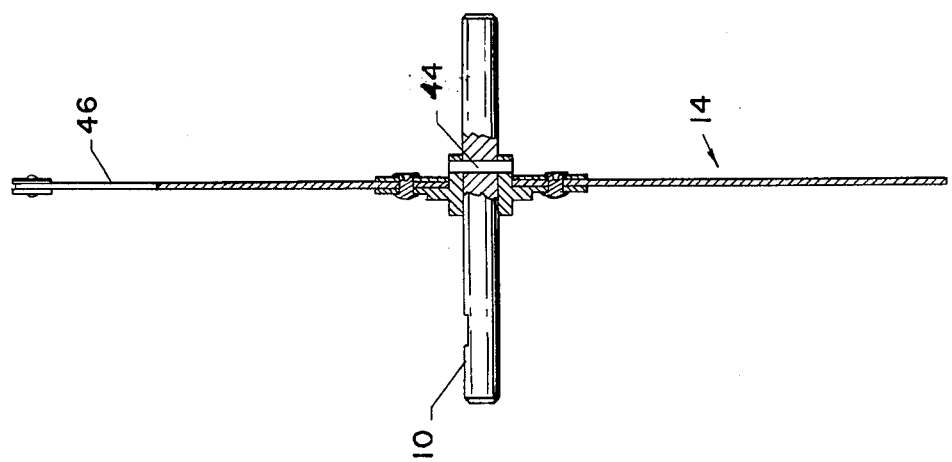

Referring to FIGS. 5 and 6, the second slide disc 14 is shown. Disc 14 is positively fastened to shaft 10 by means of a pin 44 so as to be rotatable therewith. Slide disc 14 defines a plurality of slide apertures disposed around its periphery as exemplified at 46.

Figure 8:
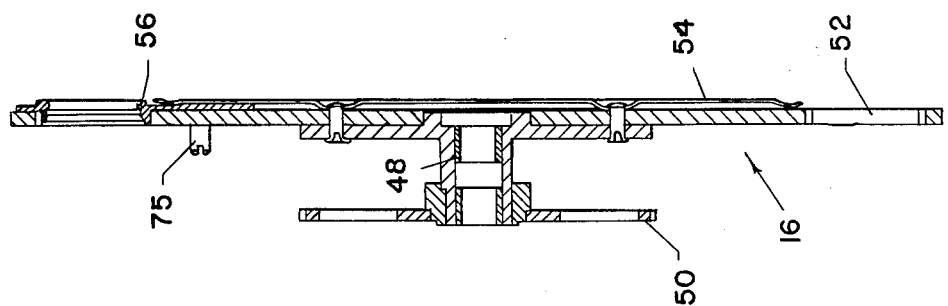
FIGS. 7 and 8 are end and side views respectively of another part of the apparatus shown in FIG. 1.
Figure 7:
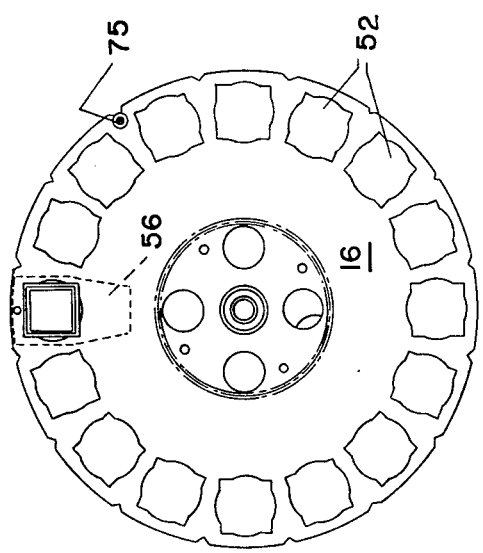

The third slide disc 16 is shown in detail in FIGS. 7 and 8. Disc 16 includes an integral shaft bearing 48 which in turn is integral with a gear 50, the gear 50 and bearing 48 being coaxial with disc 16 and rotatable about shaft 10. Disc 16 also defines a plurality of slide apertures 52 disposed around its periphery. A spring clip 54 is suitably fastened to disc plate 16 and provides a biasing force against plate 16 so as to hold slides which are inserted over the apertures 52 to the plate 16. An example of such a slide is shown at 56. A similar spring clip may be included on any of the other disc plates 12 and 14.

Figure 2:
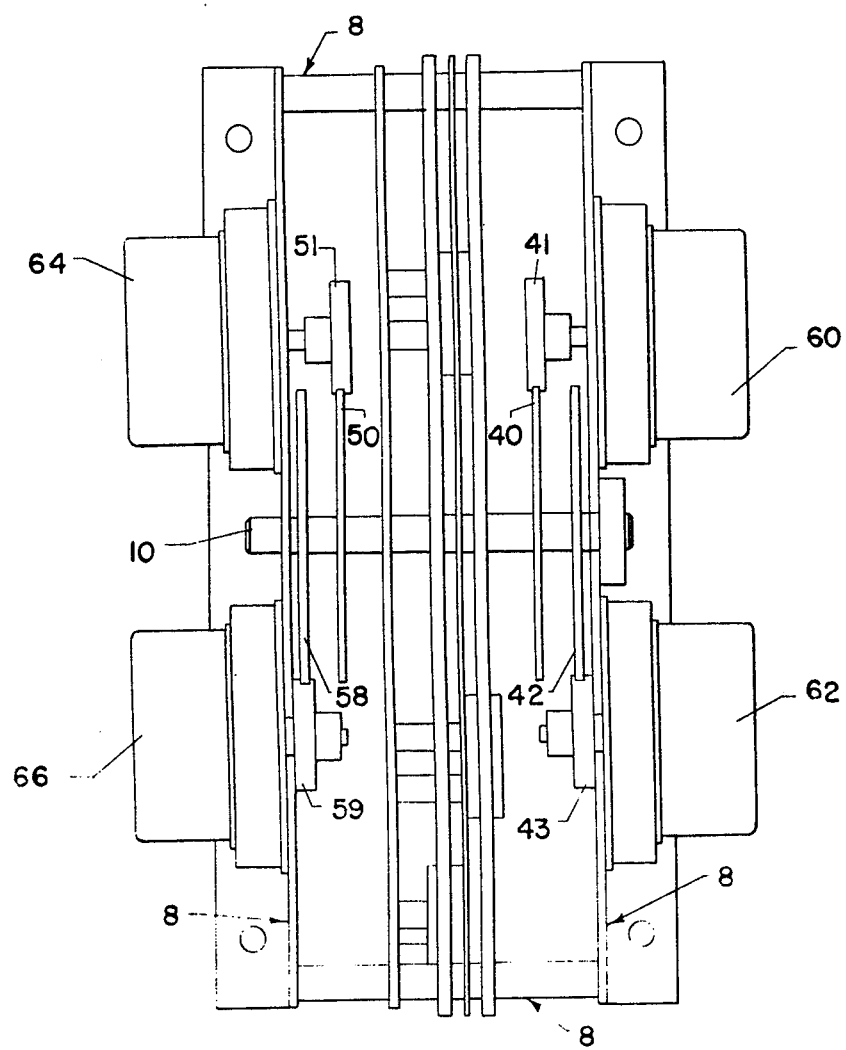
FIG. 2 is a top view of the apparatus shown in FIG. 1.

Referring again to FIGS. 1 and 2, showing discs 12, 14 and 16 in their relative positions, it will be more clearly seen that discs 12 and 16 are rotatable relative to shaft 10 and that disc 14 is fastened to shaft 10. A gear 58 is also fastened to shaft 10. A plurality of motors 60, 62, 64, 66 are mounted relative to frame 8 as shown in FIG. 2. These motors have respectively mounted thereto pinions 41, 43, 51, 59. Pinion 41 is disposed in driving relationship to gear 40. Pinion 43 is in driving relationship to gear 42. Pinion 51 is in driving relationship to gear 50. Pinion 59 is in driving relationship with gear 58. That is, motor 60 controls, through gear 40, the rotation of cells 23. Motor 62 through gear 42 drives disc 12 on shaft 10. Motor 64 through gear 50 drives disc 16 on shaft 10. And motor 66 through gear 58 drives shaft 10 and disc 14.

In FIGS. 3, 5 and 7, it will be seen that discs 12, 14 and 16 respectively have notched cam surfaces around their peripheries. The significance of these cam surfaces becomes apparent in FIG. 9. There is biased against each of these peripheral disc surfaces a pair of cam operated switches 68. Switches 68 are fixedly mounted on frame 8. When cam follower 62 of each of these switches 68 is depressed, that is to say within one of the recesses on the cam surface, the associated switch 68 is open, breaking the circuit and interrupting current.

There is biased against each of these peripheral disc surfaces a pair of cam operated switches 68, which are conveniently mounted on frame 8. When a cam follower 72 of a switch is depressed activating the associated switch, a signal is sent to control circuit 80 e.g. at up/down counter 82 incoming on line 84. It will be noted that there are three control circuits labeled 80 and 80' in the illustrated embodiment, one circuit being associated with each of the three discs 12, 14 and 16. It should be noted from the subsequent description that the circuits 80 and 80' differ slightly, for their essentially similar functions. Control circuit 80' for dial 14 uses additional components in the counting circuit because of the different number of apertures in that dial. The relative position of each disc 12, 14 and 16 is predetermined to counters 82 and 82' such that rotation of a disc and actuation of a switch 68 codes counter 82, 82' to indicate the relative rotation of each disc from a zero or originating point.

In the illustrated embodiment, this zero position is chosen to be the open aperture positions on each disc 12, 14 and 16.

Since the apertures of the discs 12, 14 and 16 are disposed one at a time in optical axis 7, it will be appreciated that there will always be one slide aperture of each disc aligned with axis 7 when motion stops. This means that, to project a given slide in a given disc without interference, the other two apertures of the other two discs which lie in the optical axis must be clear of target. Accordingly, in each of the discs 12, 14 and 16, there must be at least one clear aperture. In order that the projection lens 5 can focus on targets in disc 16, as well as disc 12, focus is made at the plane of disc 12 and block of glass mounted in the clear aperture of disc 12, one block of glass of a thickness for focusing disc 16.

Referring back to FIG. 9, in each of the control circuits 80, a counter 82 (such as synchronous up/down four-bit binary counter, e.g. Texas Instruments, Inc. SN74191) is connected to detent switch 68 for its respective disc, 12, 14 and 16. The output of the up/down counters 82, 82' is supplied to logic circuit 86. In the illustrated embodiment logic circuit 86 is a four bit binary full adder such as Texas Instruments, Inc. SN7483.

Logic circuit 86 also receives input from the slide selection keyboard 88 via individual selector switches 90 and latch and multiplexer circuits 92. In the illustrated embodiment SN7475 are used as bi-stable latches and the multiplexers are SN74150 and 74151 (for 80').

As previously mentioned, since dial 16 includes a different number of apertures than the other dials, its counting circuit is modified. In the present embodiment, the counter includes J-K flip flops, exclusive OR gates and AND gates interconnected as known in the art to form a synchronous up/down three bit binary counter with a maximum count of five. Elements such as SN7473, SN7486, SN7408 may be used, interconnected in the known manner as illustrated in descriptive literature supplied by manufacturers.

Logic circuits output to motor control circuits 94 to provide the drive information for dial motors 62, 64 and 66. These control circuits include AND, NAND and NOR gates connected to inverters in known manner to provide the drive signals to the synchronous motors (62, 64, and 66) depending upon the difference of the outputs of the up/down counters 82, 82' and the latch and multiplexer circuits 92. Gates from Texas Instruments, Inc. such as SN7404, SN7451, SN7410, SN7420 may be used in the known manner and according to manufacturers' directions.

Figure 9:
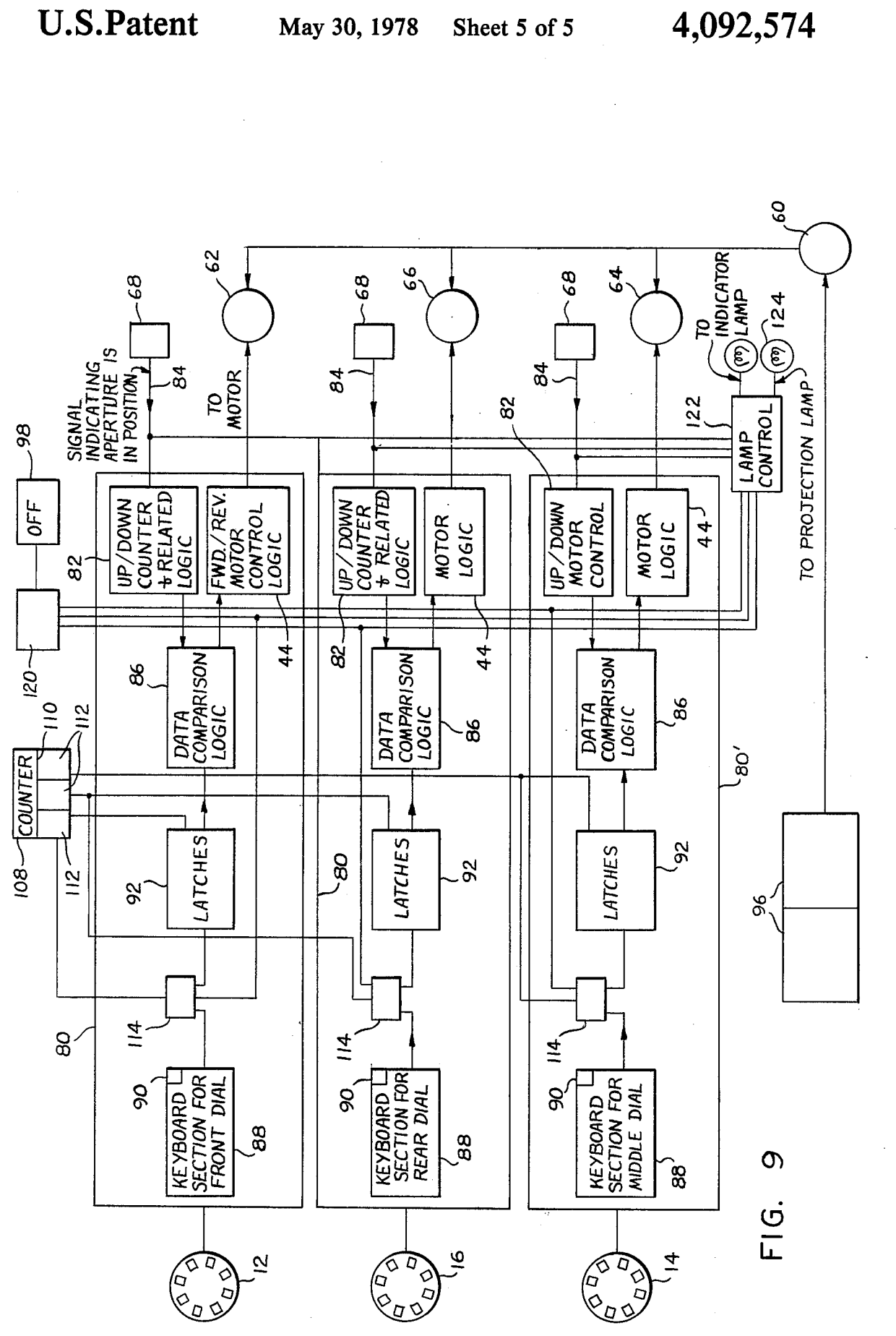

Additionally shown in FIG. 9, and being part of the overall control of the chart projector, are switches 96 which are directly connected to motor 60 to cause rotation of cells 23 containing the paraboline chart 24 and astigmatic chart 26. These switches 96 cause, upon actuation, rotation of the chart cells 23 in either clockwise or counter-clockwise directions.

Each control 80 contains an interconnection to an on/off switch 98, which, in the illustrated embodiment, contains a latch function directly coupled to motor control circuit 94, intermediate the comparison circuit 86 and the motor control circuit 94. Actuation of the off switch causes the discs 12, 14 and 16 to index to a predetermined location (the open aperture position).

By way of further description, counter circuit 108 contains a free running clock 110 which cycles the counter 112 to generate binary numbers which the multiplexers 114 use to sample the individual keys 90 in keyboard 88 perhaps as much as once every 428 microseconds.

Depressing a key 90 on the keyboard 88 results in multiplexer 114 setting its respective latches 92 to produce the corresponding binary number at the output of the latches.

Up/down counter 82 counter 82 is clocked each time a detent switch 68 closes on a respective disc so that the counters give the position of the disc — zero being home.

The number forming the output of a set of latches 92 resulting from a switch 90 selection on a keyboard 88 is subtracted by its comparison circuit 86 from the output of the up/down counter 82 and subsequently a motor 62, 64, 66 is enabled, if the output of comparison circuit 86 is not zero. In the preferred embodiment, the direction of the motor rotation is determined by the most significant bit of information in the comparison circuit, and coded such that direction of travel is toward the shortest route. When the output of a comparison circuit 86 is zero, the counters 82 and the latches 92 are said to be a coincidence.

When the front disc 12 or rear disc 16 leaves coincidence, it "keys" a zero into the multiplexer of the opposite disc in order to send the latter to its home position an open aperture. This ensures the selected slide being presentable from the selected disc 12 or 16 through the open aperture of disc 16 or 12.

The "off" switch 98 sets the "off" latch 120 to "key" a zero into the three multiplexers (114) and also drives the discs 12, 14, and 16 until they reach home. The "off" latch is also set at "power turn on".

The control circuitry for the chart projector also includes a lamp control 122 which receives its input from the logic circuits 86. The lamp control circuit includes two SCR optical relay combinations each switching one half the A-C supply wave to give three possible lamp indications. The relay combinations are interconnected in the illustrated embodiment such that the lamp 124 is fully illuminated when a selected slide from any disc 12, 14, and 16 is fully indexed at a selected position. When a keyboard switch 90 is pressed and the discs are being indexed, the lamp 124 goes to half bright. When the projector is turned off, the light goes out.

Others skilled in the art may recognize that modifications to the described embodiments may be made which, however, lie within the concept and scope of the present invention. Accordingly, it is intended that the invention be not limited by the details by which it has been described but, however, will be measured by the following claims:

What is claimed is:

1. In a slide projector having a plurality of rotatable coaxial discs, each defining a plurality of slide apertures disposed peripherally therearound and positionable one at a time in the optical axis of said projector, each of said discs being interconnected to a driving motor for rotation of said discs, and control means to effect motor operation in continuous and incremental modes of rotation in response to slide selection at a master keyboard, wherein the improvement comprises:
   a keyboard selection switchboard dedicated to each of said discs,
   a keyboard switch on said board dedicated to each slide aperture on said disc,
   multiplexing means dedicated to each of said switchboards to sample each keyboard switch on said board,
   free running counting means for sampling the actuated state of said switches,
   latching circuit means connected to said multiplexing means for recording actuation of said switches,
   counting means interconnected to said discs for recording the relative position of each of said discs,
   comparison means for comparing the output of said latch circuit means and said disc counting means, said comparison means being interconnected to said driving motor whereby said motor is operated in response to the output of said comparison means.

2. The improvement according to claim 1 wherein said driving motor is a reversible motor and said comparison means is interconnected to motor control circuit means for driving said motor in the direction of rotation of least rotation for the selected slide.

3. The improvement according to claim 1 including off/on switch and latching means, said means being interconnected to said control means to effect motor operation whereby actuation of said off/on switch causes said discs to rotate to a preselected index position.

* * * * *